United States Patent [19]

Shively

[11] 4,336,265
[45] Jun. 22, 1982

[54] METHOD OF INCREASING FEED EFFICIENCY IN SWINE

[75] Inventor: Jesse E. Shively, Terre Haute, Ind.
[73] Assignee: Pfizer Inc., New York, N.Y.
[21] Appl. No.: 204,731
[22] Filed: Nov. 6, 1980
[51] Int. Cl.³ ............................................. A61K 31/35
[52] U.S. Cl. .................................................. 424/283
[58] Field of Search ...................................... 424/283

[56] References Cited

U.S. PATENT DOCUMENTS

| | | | |
|---|---|---|---|
| 3,839,557 | 10/74 | Raun | 424/115 |
| 3,857,948 | 12/74 | Tanaka et al. | 424/283 |
| 4,009,262 | 2/77 | Boeck et al. | 424/123 |
| 4,192,887 | 3/80 | Cloyd et al. | 424/283 |
| 4,260,631 | 4/81 | Dost et al. | 424/283 |

FOREIGN PATENT DOCUMENTS 2349329  11/77  France.

OTHER PUBLICATIONS

*Dtsch. Tierarztl. Wschr.* 86, 390–394 (1979).

*Primary Examiner*—Frederick E. Waddell
*Attorney, Agent, or Firm*—Charles J. Knuth; Peter C. Richardson; James H. Monroe

[57] ABSTRACT

Oral administration of salinomycin and 4-methyl-salinomycin to swine in the grower and finisher phases of their life cycle results in an increase in the efficiency of feed utilization.

6 Claims, No Drawings

METHOD OF INCREASING FEED EFFICIENCY IN SWINE

BACKGROUND OF THE INVENTION

The present invention relates to a method of increasing the efficiency of feed utilization in swine during the grower and finisher phases of their growth cycle.

It is well known that the oral administration of certain organic compounds, for example 3-(2-quinoxalinylmethylene)carbazate-$N^1,N^4$-dioxide, and many antibiotics increases either the rate of growth or the efficiency of feed utilization in swine, and in some cases both effects are observed. While French Pat. No. 2,349,329 discloses the use of salinomycin for the treatment of gastrointestinal infections and for growth promotion in swine, it has heretofore been understood in the art that the effect of antibiotics on the rate of growth and efficiency of feed utilization in swine decreases with increasing age and size of the animals and is economically most significant in the starter phase of the animal's life i.e. from the time the pig is weaned to about 25 kg in weight. Accordingly, it has not heretofore been possible to fully realize the potential economic benefits of increasing the efficiency of feed utilization in swine during the later stage of the grower phase (i.e. from about 35 kg to about 60 kg body weight) and during the finisher phase (i.e. from about 60 kg to market weight) of the growth cycle by administration of an antibiotic.

SUMMARY OF THE INVENTION

It has now been found that oral administration of salinomycin or 4-methylsalinomycin unexpectedly significantly increases the efficiency of feed utilization in swine during the grower and finisher phases, especially in pigs weighing more than about 35 kg. Contrary to the effects heretofore experienced with other antibiotics used for growth promotion in swine, such as Tylosin and Virginiamycin, the increase in the efficiency of feed utilization is significantly greater during the grower and finisher phases of the growth cycle than during the starter phase. In particular, a significant increase in the efficiency of feed utilization is realized by the addition of salinomycin or 4-methylsalinomycin to swine in the finisher phase of the growth cycle i.e. in animals weighing more than about 60 kg.

Accordingly, the present invention comprises a method of increasing the efficiency of feed utilization by swine comprising orally administering to a pig weighing at least about 35 kg, preferably at least about 60 kg, an effective amount of a compound selected from salinomycin, 4-methylsalinomycin and the physiologically acceptable esters and salts thereof. Preferably the compound is administered in the feed of the animals in an amount from about 5 to 100 ppm, preferably from about 20 to 60 ppm, based on the total weight of the feed.

The present invention also embraces swine feed compositions comprising a swine feed ration and a feed efficiency increasing amount of 4-methylsalinomycin.

DETAILED DESCRIPTION OF THE INVENTION

The compounds useful in the present method for increasing the efficiency of feed utilization in swine during the grower and finisher phases of their growth cycle are salinomycin, 4-methylsalinomycin, the physiologically acceptable salts and esters thereof, or mixtures of these compounds. Suitable salts include the alkali metal salts, for example the sodium or potassium salts, the alkaline earth metal salts, such as the calcium or magnesium salts, and the ammonium salts. Suitable esters include the lower alkyl esters having from 1 to 6 carbon atoms. Salinomycin for use in the present process may be prepared by methods well known in the art, for example, as described in U.S. Pat. No. 3,857,948. Similarly, the preparation of 4-methylsalinomycin is described in U.S. Pat. No. 4,009,262. The active compound may be used in the present method either as the isolated compound or in a form such as the mycelial filter cake which contains the active compound.

Salinomycin, 4-methylsalinomycin, or salts or esters thereof, when administered to swine during the grower and finisher phases in accord with the present process increase the efficiency of feed utilization i.e. increase the weight of the animal gained per pound of feed consumed. Efficiency of feed utilization should be distinguished from the rate of growth, which as used in the present specification refers to the increase in weight of the animal per unit of time, regardless of the amount of feed consumed. The salinomycin or 4-methylsalinomycin, or a salt or ester thereof, is administered orally to swine during the grower phase, particularly to pigs weighing more than about 35 kg and in the finisher phase when the pig will weigh at least about 60 kg. The active compound may be orally administered by a variety of methods, but is preferably included in the feed of the swine. The effective dosage amount of the active compound is from about 0.15 to about 5 mg/kg body weight of the animal/day, preferably about 0.8 to about 3.0 mg/kg/day. Concentrations of the active ingredient in the feed to achieve the desired dosage amount will be in the range of about 5 ppm to about 100 ppm, preferably from about 20 ppm to about 60 ppm, based on the total weight of the feed. Such admixtures with the feed are readily prepared by thoroughly mixing a suitable amount of the active compound, with the solid feed, for example grains, such as corn, sorghum, wheat, barley, oats and the like, soya meal, fish meal, etc. together with, if desired, other optional additives conventionally employed in the art, for example trace minerals and vitamins. As recognized by those skilled in the art, swine feeds are different from other feeds, such as cattle feeds. Typically, swine feeds do not contain roughages such as, for example, corn cobs or cottonseed hulls. Furthermore, they do not generally contain urea as a source of non-protein nitrogen. If desired, the active salinomycin compound may be incorporated in a concentrate or premix which is then combined with the animal feed to provide the desired dosage amount. Such premixes or concentrates may contain from about 0.5 weight percent to about 20 weight percent, preferably from about 5 to 10 weight percent of the active ingredient and a physiologically acceptable solid or liquid carrier or diluent. Suitable solid materials for this purpose include, for example, soya meal, corn meal, grain husks, calcium carbonate and the like. Liquid diluents include water, physiologically acceptable organic solvents and the like. If desired, such concentrates or premixes may contain other ingredients, such as trace minerals or vitamins. Such concentrates or premixes are then added to the feed of the animal in an amount sufficient to provide the desired concentration in the resulting feed mixture and to provide the desired dosage amounts in the range previously described.

While it is preferred to administer salinomycin or 4-methylsalinomycin in the feed of the animals as described above, it will be understood that other methods of oral administration may also be employed. For example, the compound may be administered in a physiologically acceptable veterinary preparation, for example as a bolus, powder, solution, paste, syrup, or the like, formed by combination of the active salinomycin compound in an amount sufficient to give the desired dosage amount and a physiologically acceptable solid or liquid diluent or carrier.

The present invention is illustrated by the following examples. However it should be understood that the invention is not limited to the specific details of these examples. In the swine growing-finishing tests described in these examples nutritionally adequate basal rations for the weights of the pigs were fed on an ad libitum basis. The basal ration refers to the total feed intake of the pigs which was in the form of a complete feed ration into which was incorporated in one composition all of the elements constituting the dietary requirements of the animal, or may be regarded as the sum of all elements contained in various feedstuffs, concentrates, supplements, mineral, vitamin or medicated premixes or the like which are fed to the animal. The composition and calculated analysis of typical basal rations which may be fed as a complete feed to growing-finishing swine are as shown below in Table 1.

TABLE 1

Basal Swine Rations

| Ingredient | 14% Protein Ration (Fed 35 to 60 kg weight) | 13% Protein Ration (Fed 60 to 91 kg) |
|---|---|---|
| Ground sorghum, 9% protein | 72.6 | 69.9 |
| Soybean meal, 44% protein | 10.0 | 9.0 |
| Rice bran, 13% protein | 7.5 | 12.0 |
| Fishmeal, menhaden, 60% protein | 2.0 | — |
| Meat and bone meal 50% protein | 2.0 | 2.5 |
| Cane Molasses | 4.0 | 5.0 |
| Soft rock phosphate; 16.5% Ca, 9% P | 0.6 | — |
| Limestone, 38% Ca | 0.3 | 0.6 |
| Iodized salt | 0.4 | 0.4 |
| Vitamin premix[a] | 0.5 | 0.5 |
| Trace mineral premix[ab] | 0.1 | 0.1 |
| TOTAL | 100.0 | 100.0 |

14% Protein

TABLE 1-continued

Basal Swine Rations

| Calculated Analyses | Ration (Fed 35 to 60 kg weight) | 13% Protein Ration (Fed 60 to 91 kg) |
|---|---|---|
| Protein | 14.2 | 13.2 |
| Fat | 3.3 | 3.7 |
| Fiber | 3.2 | 3.7 |
| Calcium | 0.59 | 0.56 |
| Phosphorus | 0.61 | 0.58 |
| Metabolizable energy (kcal/kg) | 2979 | 2953 |

[a]contributes the following levels of vitamins per kilogram of ration: vitamin A, 4410 I.U; vitamin D, 441 I.U.; vitamin E, 11. I.U.; vitamin K, 2.2 mg; niacin, 26.4 mg; riboflavin, 3.3 mg; pantothenic acid, 15.5 mg; choline chloride, 1100 mg; vitamin $B_{12}$, 22 mcg.
[b]Contributes the following levels of trace mineral in parts per million: manganese, 120; iron, 40; copper, 4; iodine, 2.4; cobalt, 0.4; zinc, 100; selenium, 0.1

EXAMPLE 1

This test demonstrates the effect of salinomycin at 50 ppm of the ration from about 35 kg body weight to market weight upon efficiency of feed utilization (expressed as feed efficiency) following feeding of either carbadox or a combination of carbadox and salinomycin from weaning to about 35 kg.

Pigs used in this test were 90 Conner Prairie-Hampshire-Yorkshire crossbred pigs. They were weaned and allotted to three treatment groups of 30 pigs each (three male castrates and three females in each of five pens) when they weighed an average of about 10 kg. Allotment of pigs was on the basis of initial weight, conditioning period weight change and litter of origin. They were fed their pretest treatment regimens in nutritionally adequate diets for a period of about 39 days or until they weighed an average of approximately 35 kg. At that time, pigs previously receiving no feed additive remained on a nonmedicated diet and pigs formerly fed carbadox or carbadox plus salinomycin were fed typical basal rations containing salinomycin at 50 ppm.

During the salinomycin feeding test period, all pigs were individually weighed and pen feed comsumption and feed efficiency were calculated at various interim periods and at trial termination. For the entire feeding period all pens of pigs were housed in an open-front shed which covered about one third of the solid concrete floored pens. Pigs were removed from the study as individual pens reached an average weight of about 91 kg.

Results of this test, which were summarized during the periods when pigs weighed approximately 35 and 60 kg to market weight, were as shown in Table 2.

TABLE 2

Performance Data from 35 and 60 kg to Market Weight for Pigs Fed Salinomycin at 50 ppm of the Ration

| Treatment Additive | Average Weight kg Initial | Average Weight kg Final | Average Days on Test | Average Daily Gain (G) kg | Average Daily Gain (G) % Imp. | Average Daily Feed, (F) kg | Feed Efficiency F/G | Feed Efficiency % Imp. |
|---|---|---|---|---|---|---|---|---|
| ~ 35 kg to Market Weight | | | | | | | | |
| Nonmedicated control | 32.0 | 91.0 | 73.2 | 0.81 | — | 2.86 | 3.56 | — |
| Salinomycin, 50 ppm* | 35.1 | 91.2 | 68.4 | 0.82 | 1.8 | 2.75 | 3.35 | 6.0 |
| Salinomycin, 50 ppm** | 34.9 | 91.8 | 70.2 | 0.81 | 0.8 | 2.76 | 3.40 | 4.6 |
| ~60 kg to Market Weight | | | | | | | | |
| Nonmedicated control | 57.6 | 91.0 | 42.0 | 0.80 | — | 3.10 | 3.89 | — |

TABLE 2-continued

Performance Data from 35 and 60 kg to Market Weight for Pigs Fed Salinomycin at 50 ppm of the Ration

| Treatment Additive | Average Weight kg | | Average Days on Test | Average Daily Gain (G) | | Average Daily Feed, (F) kg | Feed Efficiency | |
|---|---|---|---|---|---|---|---|---|
| | Initial | Final | | kg | % Imp. | | F/G | % Imp. |
| Salinomycin, 50 ppm* | 60.9 | 91.2 | 37.2 | 0.81 | 2.2 | 3.01 | 3.70 | 5.3 |
| Salinomycin, 50 ppm** | 61.1 | 91.8 | 39.0 | 0.80 | −0.7 | 2.98 | 3.76 | 3.5 |

*Pigs fed carbadox, 50 ppm, from 10 kg to 35 kg
**Pigs fed carbadox, 50 ppm, plus salinomycin, 50 ppm, from 10 kg to 35 kg

EXAMPLE 2

This test compared the effect of salinomycin at 25 ppm and tylosin at 22 ppm of the ration upon the efficiency of feed utilization of growing-finishing swine. Tylosin has previously been identified and is marketed as an additive for improving weight gain and improving feed efficiency in swine.

Animals used in this test were 96 Large White weaner pigs. When they weighed approximately 25 kg, they were randomly allotted into three treatment groups of 32 pigs. Four castrate and four female pigs were placed in each of four pens per treatment group. All pigs were housed in a completely enclosed building in pens with solid concrete floors for the duration of the study.

The test levels of salinomycin (25 ppm) and tylosin (22 ppm) were incorporated into nutritionally adequate basal diets. Pigs were individually weighed and feed consumption and feed efficiency were calculated at various interim periods and at the termination of the trial when pigs weighed approximately 90 to 95 kg.

Data for this test were summarized during the periods from approximately 35 kg and 60 kg body weight to final weight. A summary of these data is as appears in Table 3 below.

EXAMPLE 3

This test evaluates the efficiency of feed utilization (expressed as feed efficiency) in swine when 25 ppm salinomycin was added to the basal ration and to compare the performance observed with swine fed no additive or with virginiamycin, an additive known to improve weight gains and feed utilization.

Experimental animals used in the test were 72 Large White/Landrace pigs that had been grown on a common feed additive which had been incorporated into nutritionally adequate diets. When pigs reached an average weight of approximately 24 kg, they were alloted to the three treatment groups of 28 pigs each (four pens of seven pigs with a sex ratio of either three or four females and intact males) on the basis of initial weight. Pigs were housed in a completely covered shed with concrete floors (⅓ of pen slatted) for the duration of the study.

All pigs were individually weighed and pen feed consumption and feed efficiency calculated at various periods during the trial and at the trial termination.

Results of this test, which were summarized during the periods when pigs weighed approximately 35 and 60 kg to market weight, were as shown in Table 4 below.

TABLE 3

Performance Data from Approximately 35 and 60 kg to Market Weight for Pigs Fed Rations Containing Salinomycin at 25 ppm or Tylosin at 22 ppm.

| Treatment Additive | Average Weight kg | | Average Days on Test | Average Daily Gain (G) | | Average Daily Feed, (F) kg | Feed Efficiency | |
|---|---|---|---|---|---|---|---|---|
| | Initial | Final | | kg | % Imp. | | F/G | % Imp. |
| ~ 35 kg to Market Weight | | | | | | | | |
| Nonmedicated control | 31.2 | 91.2 | 73.5 | 0.82 | — | 2.51 | 3.07 | — |
| Salinomycin, 25 ppm | 36.9 | 93.2 | 63.0 | 0.90 | 9.4 | 2.64 | 2.94 | 4.4 |
| Tylosin 22 ppm | 33.6 | 96.8 | 73.5 | 0.86 | 5.2 | 2.69 | 3.12 | −1.6 |
| ~ 60 kg to Market Weight | | | | | | | | |
| Nonmedicated control | 53.1 | 91.2 | 45.5 | 0.84 | — | 2.71 | 3.23 | — |
| Salinomycin, 25 ppm | 61.8 | 93.2 | 35.0 | 0.90 | 7.5 | 2.79 | 3.09 | 4.5 |
| Tylosin, 22 ppm | 57.3 | 96.8 | 45.5 | 0.87 | 3.6 | 2.89 | 3.32 | −2.7 |

TABLE 4

Performance Data from 35 and 60 kg to Market weight for Pigs Fed Rations Containing Salinomycin at 25 ppm or Virginiamycin at 20/10 ppm.

| Treatment Additive | Average Weight kg Initial | Average Weight kg Final | Average Days on Test | Average Daily Gain (G) kg | Average Daily Gain (G) % Imp. | Average Daily Feed, (F) kg | Feed Efficiency F/G | Feed Efficiency % Imp. |
|---|---|---|---|---|---|---|---|---|
| ~ 35 kg to Market Weight | | | | | | | | |
| Nonmedicated control | 33.5 | 87.5 | 83 | 0.65 | — | 2.28 | 3.51 | — |
| Salinomycin, 25 ppm | 34.7 | 93.9 | 83 | 0.71 | 9.7 | 2.30 | 3.23 | 8.6 |
| Virginiamycin, 20/10 ppm* | 34.3 | 87.7 | 83 | 0.64 | −1.1 | 2.24 | 3.48 | 0.9 |
| ~ 60 kg to Market Weight | | | | | | | | |
| Nonmedicated control | 54.9 | 87.5 | 48 | 0.68 | — | 2.48 | 3.67 | — |
| Salinomycin, 25 ppm | 58.5 | 93.9 | 48 | 0.74 | 8.9 | 2.53 | 3.42 | 7.2 |
| Virginiamycin, 20/10 ppm* | 56.0 | 87.7 | 48 | 0.66 | −2.5 | 2.43 | 3.68 | −0.2 |

*20 ppm virginiamycin fed to approximately 50 kg average weight; 10 ppm virginiamycin fed from 50 kg to trial termination.

I claim:

1. A method of increasing the utilization of feed by swine comprising orally administering to a pig weighing at least about 35 kg an effective amount of a compound selected from salinomycin and 4-methylsalinomycin and the physiologically acceptable esters and salts thereof.

2. A method according to claim 1 wherein the compound is salinomycin.

3. A method according to claim 1 wherein the compound is 4-methylsalinomycin.

4. A method according to claim 1 wherein the pig weighs at least about 60 kg.

5. A method according to claim 1 wherein the compound is administered in the feed of said pig in an amount from about 5 p.p.m. to 100 p.p.m.

6. A method according to claim 5 wherein salinomycin is administered in the feed of said pig in an amount from about 20 p.p.m. to 60 p.p.m.

* * * * *